(12) United States Patent
Ganapathy

(10) Patent No.: US 8,801,644 B2
(45) Date of Patent: Aug. 12, 2014

(54) PNEUMATIC COMPRESSION GARMENT WITH NOISE ATTENUATION

(71) Applicant: Covidien LP, Mansfield, MA (US)

(72) Inventor: Premnarayan Ganapathy, Brookline, MA (US)

(73) Assignee: Covidien LP, Mansfield, MA (US)

(*) Notice: Subject to any disclaimer, the term of this patent is extended or adjusted under 35 U.S.C. 154(b) by 0 days.

(21) Appl. No.: 13/661,771

(22) Filed: Oct. 26, 2012

(65) Prior Publication Data
US 2013/0296752 A1 Nov. 7, 2013

Related U.S. Application Data

(62) Division of application No. 12/569,323, filed on Sep. 29, 2009, now Pat. No. 8,328,741.

(51) Int. Cl.
*A61F 5/00* (2006.01)
*A61F 13/08* (2006.01)
*A61F 5/34* (2006.01)
*A61H 9/00* (2006.01)
*A61F 5/01* (2006.01)
A61B 17/132 (2006.01)
A61B 17/135 (2006.01)

(52) U.S. Cl.
CPC ............ *A61H 9/005* (2013.01); *A61B 17/1325* (2013.01); *A61F 13/085* (2013.01); *A61B 17/135* (2013.01); *A61F 5/34* (2013.01); *A61H 9/0092* (2013.01); *A61F 5/0111* (2013.01); *A61H 2205/12* (2013.01); *A61H 2201/165* (2013.01)
USPC ............................................ 602/13; 128/847

(58) Field of Classification Search
USPC ....................... 602/13; 601/148–152
See application file for complete search history.

(56) References Cited

U.S. PATENT DOCUMENTS

| 3,677,300 | A | 7/1972 | King |
| 3,736,074 | A | 5/1973 | Kilbane et al. |
| 3,855,910 | A | 12/1974 | Brinton et al. |
| 3,944,084 | A | 3/1976 | Reeves |
| 3,946,735 | A | 3/1976 | DeWall |
| 4,135,500 | A | 1/1979 | Gorran |
| 4,264,282 | A | 4/1981 | Crago |

(Continued)

FOREIGN PATENT DOCUMENTS

| EP | 0897707 A2 | 2/1999 |
| GB | 2271060 A | 4/1994 |
| GB | 0217996.8 | 8/2002 |
| WO | 2005063164 A1 | 7/2005 |

OTHER PUBLICATIONS

European Search Report dated Mar. 1, 2011 from European Application No. 10182182.5, 4 pages.

(Continued)

*Primary Examiner* — Patricia Bianco
*Assistant Examiner* — Keri J Nelson
(74) *Attorney, Agent, or Firm* — John Paul Mello, Esq.

(57) ABSTRACT

A compression garment for applying compression to a part of a wearer's body includes a flexible member, an inflatable bladder defining an inflatable chamber, and a port for communication between a source of pressurized air and the inflatable chamber. The garment also incorporates noise attenuation. The noise attenuation can include noise attenuating members on an air impingement surface of the inflatable bladder.

7 Claims, 7 Drawing Sheets

(56) References Cited

U.S. PATENT DOCUMENTS

| | | | |
|---|---|---|---|
| 4,399,739 A | 8/1983 | Dean | |
| 4,418,443 A | 12/1983 | Fischer | |
| 4,435,877 A | 3/1984 | Berfield | |
| 4,450,933 A | 5/1984 | Fukuoka et al. | |
| 4,534,343 A | 8/1985 | Nowacki et al. | |
| 4,606,328 A | 8/1986 | Thoman | |
| 4,729,722 A | 3/1988 | Toth | |
| 4,872,448 A | 10/1989 | Johnson, Jr. | |
| 4,888,003 A | 12/1989 | Johnson et al. | |
| 4,911,697 A | 3/1990 | Kerwin | |
| 4,921,477 A | 5/1990 | Davis | |
| 4,991,617 A | 2/1991 | Butler | |
| 5,047,072 A | 9/1991 | Wertz et al. | |
| 5,118,262 A | 6/1992 | Kuo | |
| 5,147,243 A | 9/1992 | Inglis et al. | |
| 5,174,127 A | 12/1992 | Harper et al. | |
| 5,214,253 A | 5/1993 | Houston, Jr. | |
| 5,260,524 A | 11/1993 | Schroeder et al. | |
| 5,285,791 A | 2/1994 | Smith | |
| 5,353,525 A | 10/1994 | Grim | |
| 5,354,260 A | 10/1994 | Cook | |
| 5,449,379 A | 9/1995 | Hadtke | |
| 5,599,333 A | 2/1997 | Atkinson | |
| 5,628,306 A | 5/1997 | Kee | |
| 5,804,777 A | 9/1998 | Kim et al. | |
| 5,858,062 A | 1/1999 | McCulloh et al. | |
| 5,961,309 A | 10/1999 | Harpole et al. | |
| 5,996,731 A | 12/1999 | Czabala et al. | |
| 6,089,346 A | 7/2000 | Tredinnick et al. | |
| 6,126,393 A | 10/2000 | Arnold | |
| 6,231,009 B1 | 5/2001 | Kong | |
| 6,280,153 B1 | 8/2001 | Iversen et al. | |
| 6,340,069 B1 | 1/2002 | Wang | |
| 6,382,931 B1 | 5/2002 | Czabala et al. | |
| 6,447,491 B1 | 9/2002 | Lord | |
| 6,558,137 B2 | 5/2003 | Tomell et al. | |
| 6,579,075 B2 | 6/2003 | Lee et al. | |
| 6,623,239 B2 | 9/2003 | Sahay et al. | |
| 6,663,596 B2 | 12/2003 | Griego et al. | |
| 6,682,317 B2 | 1/2004 | Chen | |
| 6,702,880 B2 | 3/2004 | Roberts et al. | |
| 6,740,066 B2 | 5/2004 | Wolff et al. | |
| 6,743,250 B2 | 6/2004 | Renfro | |
| 6,840,746 B2 | 1/2005 | Marshall et al. | |
| 6,866,700 B2 | 3/2005 | Amann | |
| 6,935,460 B2 | 8/2005 | McCombs et al. | |
| 6,966,198 B2 | 11/2005 | Piccirilli et al. | |
| 7,070,567 B2 | 7/2006 | Mizukoshi et al. | |
| 7,141,101 B2 | 11/2006 | Amann | |
| 7,153,107 B1 | 12/2006 | Maddox, Jr. | |
| 7,431,571 B2 | 10/2008 | Kim et al. | |
| 7,452,340 B2 | 11/2008 | Cook et al. | |
| 7,967,766 B2 | 6/2011 | Ravikumar | |
| 8,328,741 B2 | 12/2012 | Ganapathy | |
| 2004/0136247 A1 | 7/2004 | Morgan et al. | |
| 2004/0261621 A1 | 12/2004 | Lindsay | |
| 2005/0067218 A1 | 3/2005 | Bristow et al. | |
| 2005/0143682 A1 | 6/2005 | Cook et al. | |
| 2006/0111655 A1 | 5/2006 | Cook et al. | |
| 2006/0251527 A1 | 11/2006 | Wester | |
| 2007/0019047 A1 | 1/2007 | Kleinert et al. | |
| 2007/0135743 A1 | 6/2007 | Meyer | |
| 2007/0276313 A1 | 11/2007 | Moorehead et al. | |
| 2007/0290012 A1 | 12/2007 | Jackman | |
| 2008/0030747 A1 | 2/2008 | Shingai | |
| 2008/0082059 A1 | 4/2008 | Fink et al. | |
| 2008/0087169 A1 | 4/2008 | Clark | |
| 2008/0103422 A1 | 5/2008 | Perry et al. | |
| 2008/0200872 A1 | 8/2008 | Isham | |
| 2009/0062703 A1* | 3/2009 | Meyer et al. | 602/13 |
| 2011/0077565 A1 | 3/2011 | Hanlon et al. | |

OTHER PUBLICATIONS

Office Action issued Mar. 1, 2011 in related U.S. Appl. No. 12/569,323, now issued as Patent No. 8,328,741—6 pages.

Response to Office Action dated Apr. 26, 2011 in U.S. Appl. No. 12/569,323, now issued as Patent No. 8,328,741—12 pages.

Final Office Action issued Sep. 6, 2011 in related U.S. Appl. No. 12/569,323, now issued as Patent No. 8,328,741—9 pages.

Amendment B and Response After Final filed Oct. 28, 2011 in related U.S. Appl. No. 12/569,323, now issued as Patent No. 8,328,741—19 pages.

Amendment C and Response After Final filed Nov. 18, 2011 in related U.S. Appl. No. 12/569,323, now issued as Patent No. 8,328,741—11 pages.

Applicant-Initiated Interview Summary mailed Nov. 29, 2011 in related U.S. Appl. No. 12/569,323, now issued as Patent No. 8,328,741—4 pages.

Amendment D and Second Supplemental Response After Final filed Dec. 6, 2011 in related U.S. Appl. No. 12/569,323, now issued as Patent No. 8,328,741—5 pages.

Office Action issued Dec. 20, 2011 in related U.S. Appl. No. 12/569,323, now issued as Patent No. 8,328,741—11 pages.

Amendment E and Response to Office Action filed Mar. 20, 2012 in related U.S. Appl. No. 12/569,323, now issued as Patent No. 8,328,741—13 pages.

Final Office Action issued May 23, 2012 in related U.S. Appl. No. 12/569,323, now issued as Patent No. 8,328,741—12 pages.

Response to Final Office Action dated Jul. 20, 2012 in related U.S. Appl. No. 12/569,323, now issued as Patent No. 8,328,741—6 pages.

Australian Exam Report in related Australian Application 201022442 dated Oct. 18, 2013, 3 pages.

* cited by examiner

PNEUMATIC COMPRESSION GARMENT WITH NOISE ATTENUATION

CROSS-REFERENCE TO RELATED APPLICATION

This application is a division of U.S. Ser. No. 12/569,323, filed Sep. 29, 2009, now U.S. Pat. No. 8,328,741, the entire contents of which are incorporated by reference.

FIELD OF THE INVENTION

The present disclosure generally relates to a compression garment configured for applying compressive forces to a portion of a wearer's body. In particular, the present disclosure relates to a means for attenuating the noise generated from air flow into an inflatable chamber of the compression garment.

BACKGROUND

Compression garments for applying compressive forces to a selected area of a wearer's body are generally employed to improve blood flow in the selected area. Compression garments in which intermittent pulses of compressed air are delivered to at least one inflatable chamber in a cuff or sleeve of the garment are particularly useful. This cyclic application of pressure provides a non-invasive method of prophylaxis to reduce the incidence of deep vein thrombosis (DVT) and the like. Patients who develop this condition often have swelling (edema) and tissue breakdown (venous stasis ulcer) in the lower leg. When DVT occurs, the valves that are located within the veins of the leg can be damaged, which in turn can cause stasis and high pressure in the veins of the lower leg. These compression devices also fund particular use during surgical recovery for patients with high-risk conditions such as obesity, advanced age, malignancy, or prior thromboembolism.

In general, a compression garment of the type described above includes a flexible member having an inflatable bladder disposed therein. The compression garment is placed around the patient's foot or other selected limb, and a pressurized fluid or air is delivered into the inflatable bladder to create pressure at the part or parts of the body in contact with the bladder. The high velocity or flow rate of the pressurized fluid/air entering the bladder produces noise that can be unpleasant to the wearer of the compression device.

SUMMARY

In one aspect, a pneumatic compression garment generally comprises a flexible member for placement on a limb of a human body. An inflatable bladder defines an inflatable chamber disposed within the flexible member. A port has an air inlet adapted for communication with a source of pressurized air and an air outlet in fluid communication with the inflatable chamber for delivery of air from the source of pressurized air into the inflatable chamber. The inflatable bladder has an air impingement surface opposing the air outlet of the port. The air impingement surface comprises a plurality of noise attenuating members for reducing noise generated by air entering the inflatable chamber and impinging against the air impingement surface.

In said aspect, the noise attenuating members may comprise protrusions projecting into the inflatable chamber.

In said aspect, the protrusions may be generally cylindrical.

In said aspect, the protrusions may be arranged in a generally symmetrical array.

In said aspect, the port may comprise a right-angle assembly comprising an elbow member defining the air outlet and a tube received in the elbow member defining the air inlet.

In said aspect, the inflatable bladder may comprise two opposing sheets of flexible air-impermeable material and the elbow member may be affixed to an outside surface of one of the sheets and be in fluid communication with the inflatable chamber for delivery of air into the inflatable chamber.

In said aspect, the noise attenuating members may be integrally foil led with one of the sheets of flexible air-impermeable material.

In said aspect, the flexible member may be configured for placement on a foot.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
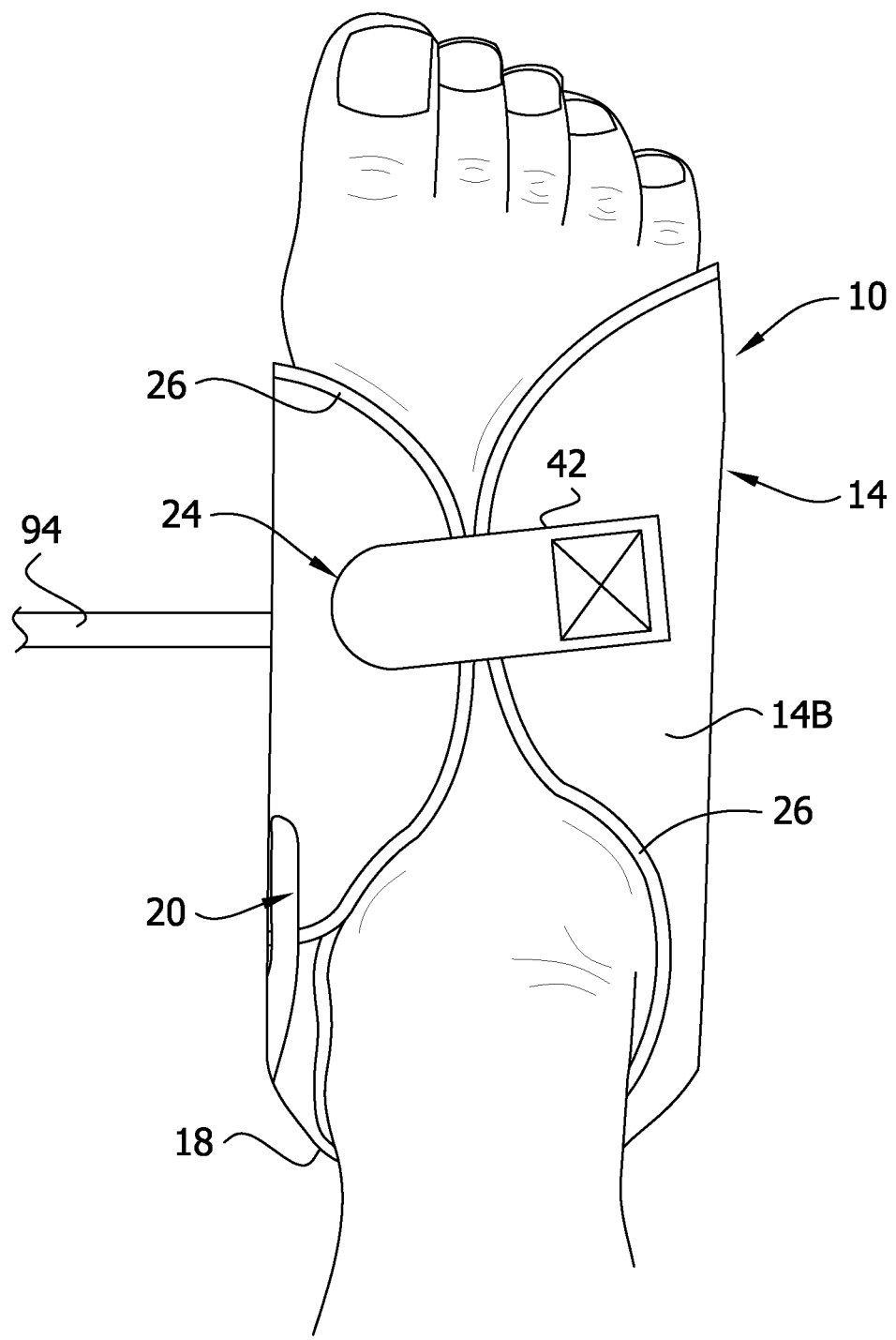
FIG. 1 is a top view of a person wearing a foot cuff of the invention.

With reference to the figures, in which like reference numerals identify identical or corresponding elements, various embodiments of the presently disclosed compression garment will now be described in detail.

Figure 2:
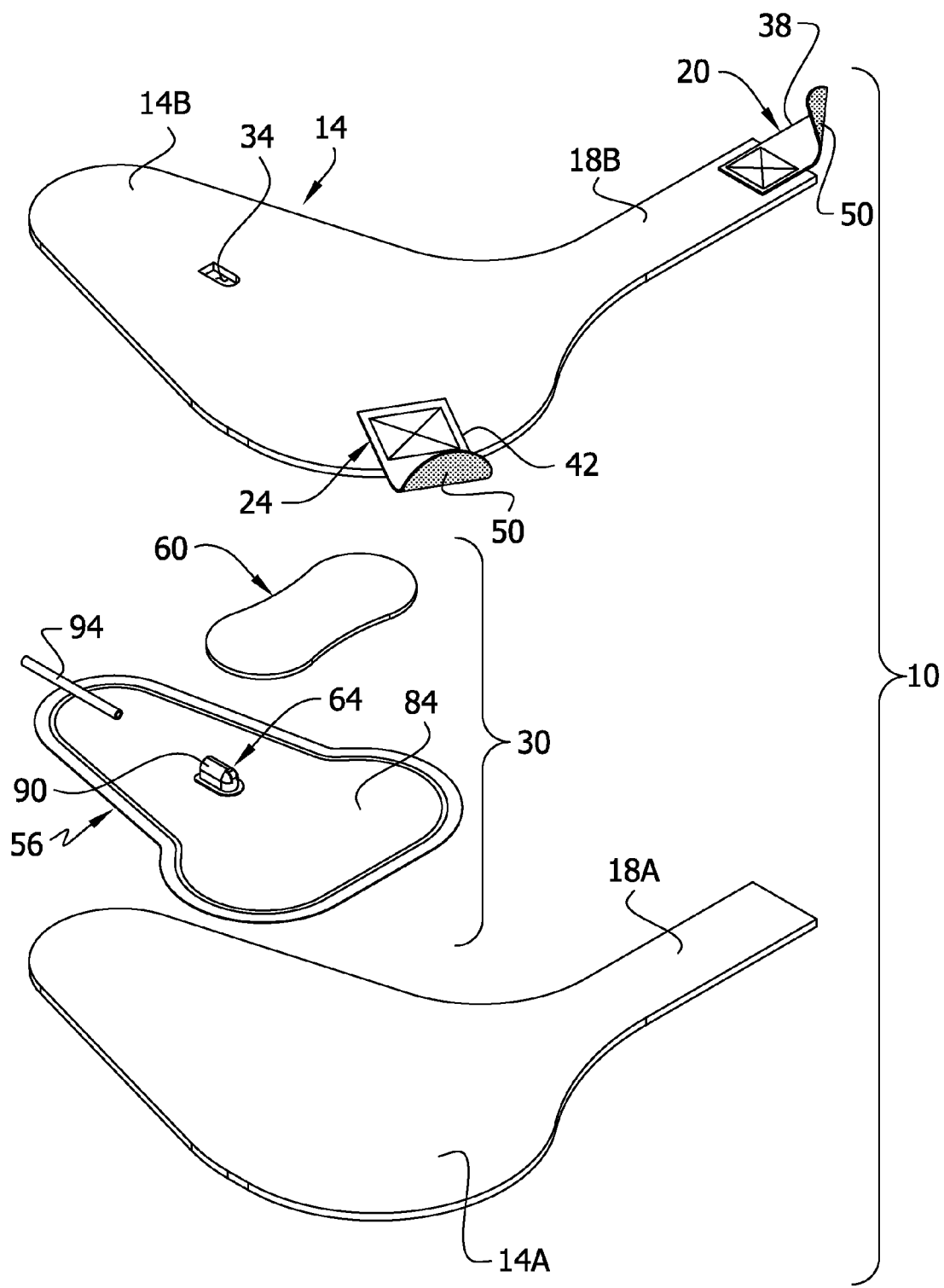
FIG. 2 is an exploded perspective of the compression foot cuff of FIG. 1.
Figure 3:
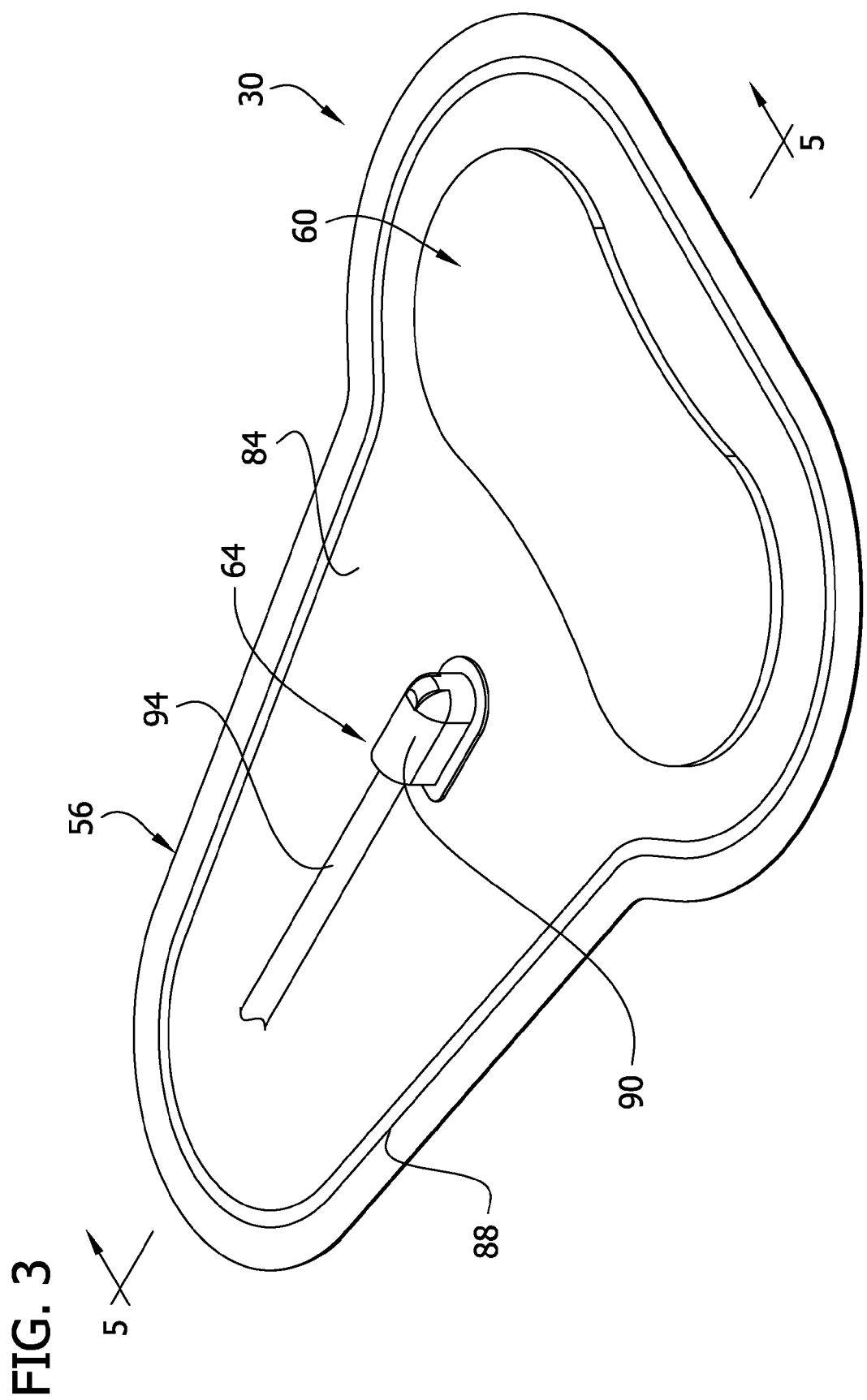
FIG. 3 is a bottom perspective of a first embodiment of a bladder assembly of the foot cuff.

With initial reference to FIGS. 1 and 2, a first embodiment of a compression garment in accordance with the present disclosure is illustrated as a foot cuff and is designated generally as 10. The foot cuff 10 is adapted for use in a compression therapy system for applying compressive pressure to a foot of a wearer, as is generally known in the art and will not be described herein. In general, the foot cuff 10 comprises a flexible member 14 configured to conform to the foot. The member 14 includes an ankle strap 18 and is secured in place by two releasable fasteners 20, 24 (described later). It is understood that the foot cuff 10 may have other configurations within the scope of the present invention. It is also understood that compression garments other than foot cuffs are within the scope of the present invention, including but not limited to leg compression sleeves, arm compression sleeves, and similar devices.

The flexible member 14 comprises an inner (contact) layer 14A and an outer layer 14B secured to one another along a line 26 generally adjacent corresponding perimeters of the layers to define an interior space for receiving and substantially enclosing a bladder assembly, generally designated 30. The inner and outer layers 14A, 14B may be fixedly secured to one another, such as by heat welding, adhesives, sewing, or other suitable ways. Alternatively, the layers 14A and 14B may be releasably secured to one another. In use, the inner layer 14A is adjacent to the wearer's foot and the outer layer 14B is located farthest from the foot. As used herein, the terms "inner" and "outer" indicate relative positions of respective components and surfaces with respect to the skin of the wearer's body part when the compression garment is secured to the body part, and as such, an "inner" component or surface is more adjacent to the skin of the body part than an "outer" component or surface.

The inner layer 14A and the outer layer 14B of the flexible member 14 include ankle strap portions 18A and 18B respectively. The ankle strap portions 18A, 18B have a longitudinally projecting configuration for wrapping about a portion of the foot adjacent to the ankle. The ankle strap portions 18A, 18B can be sewn, RF welded, or sonic welded to respective inner and outer layers 14A, 14B. However, in the illustrated embodiment, the ankle strap portions 18A, 18B are formed as one piece with the inner layer 14A and the outer layer 14B, respectively.

The inner layer 14A of the flexible member 14 is adapted for contacting the foot. In one embodiment, this layer 14A is fabricated from a chemically treated material, with wicking ability, for wicking moisture away from the skin. In some embodiments, the inner layer 14A includes a mesh-like fabric capable of wicking moisture away from the wearer's skin. Furthermore, the inner layer 14A can be faced with a soft material toward the treatment surface of the wearer. For example, the soft material can be a thin layer of open celled porous foam, napped cloth, or a layer of vapor permeable cloth. It is understood that the flexible member 14 may not include an inner layer 14A within the scope of the present invention.

Again referring to FIGS. 1 and 2, the outer layer 14B of the flexible member 14 includes an opening 34 for allowing passage of pressurized air to the bladder assembly 30. The outer layer 14B is configured for providing an attachment surface for a hook and loop feature of the foot cuff 10, as will be described in more detail below. Moreover, the outer layer 14B comprises a soft material for cushioning the top portion of the foot and may be fabricated from similar materials as the inner layer 14A and in similar dimensions therewith for corresponding geometry. Alternatively, the outer layer 14B may be fabricated from a laminated material, such as, for example, Sontara® fabric, open cell urethane foam, or loop fabric. It is understood that the foot cuff 10 may not include an outer layer 14B within the scope of the present invention.

The releasable fasteners 20, 24 are positioned on and attached to the outer layer 14B of the foot cuff for securing the foot cuff 10 around the foot. The first fastener 20 comprises a strap 38 attached to the ankle strap portion 18B of the outer layer 14B of the foot cuff 10, and the second fastener 24 comprises a strap 42 attached to a surface of the outer layer 14B. Both straps 38, 42 have hook elements 50. In use, when the ankle strap 18 is wrapped about the back of the foot, the hook elements 50 on the straps engage loop elements (not shown) on the outer layer 14B of the foot cuff 10 to secure the cuff on the foot, as will be understood by those skilled in the field familiar with foot cuffs. The releasable fasteners 20, 24 may have tabs (not shown) without fastening material thereon to provide convenient gripping locations on the hook fasteners so that the practitioner can readily separate the hooks 50 from the outer layer 14B.

Referring to FIGS. 2-5, the bladder assembly 30 is enveloped and enclosed by the flexible member 10. The assembly 30 comprises an inflatable bladder 56, a substantially rigid sole 60, and a port 64 having an air inlet 68 adapted for communication with a source of pressurized air (not shown) and an air outlet 72 in communication with an inflatable chamber 76 defined by the bladder. The various components of the bladder assembly 56 are described below.

Figure 4:
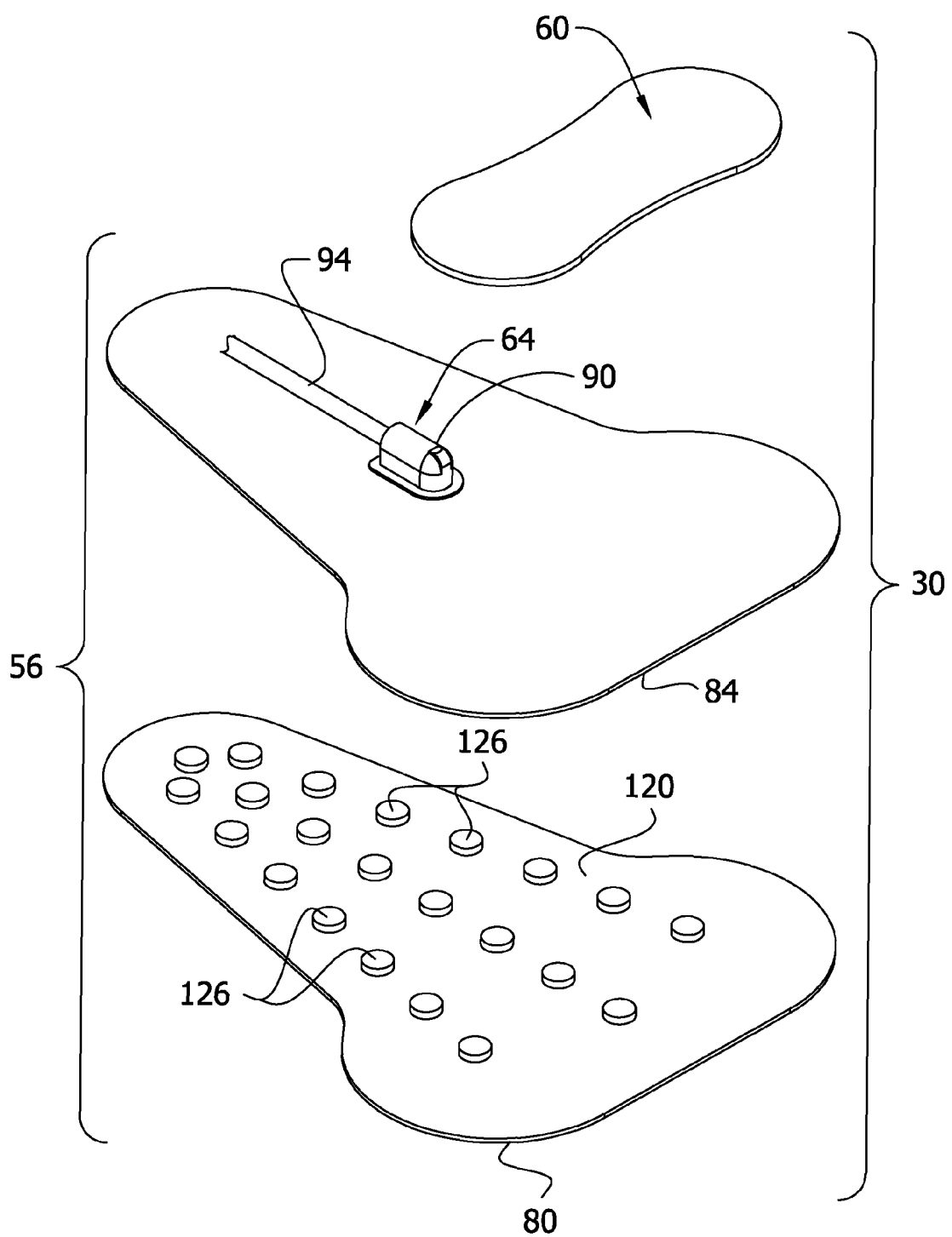
FIG. 4 is an exploded view of components of the bladder assembly of FIG. 3 showing a first embodiment of a noise attenuating means in accordance with the present disclosure.
Figure 5:
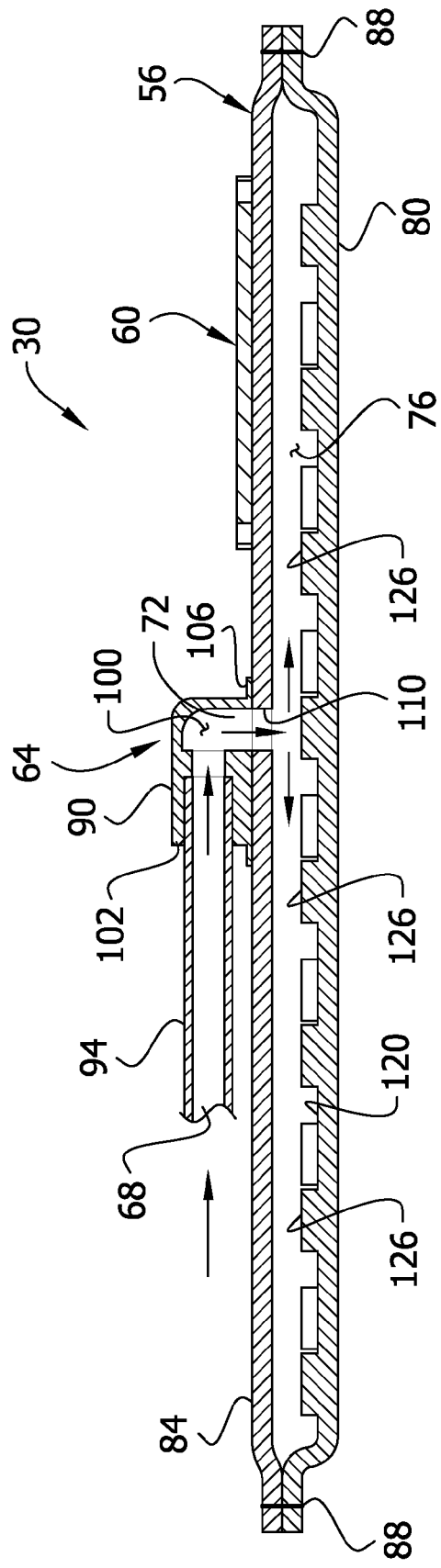
FIG. 5 is a sectional view of the bladder assembly taken along the line 5-5 in FIG. 3 showing noise attenuating members on an air impingement surface of the bladder.

Still referring to FIGS. 2-5, the bladder 56 includes inner and outer opposing sheets 80, 84 of flexible air-impermeable material (e.g., PVC) joined together in a suitable manner along a line 88 adjacent to their peripheries to define the inflatable chamber 76 (FIG. 5). As best illustrated in FIG. 2, the bladder 56 is positioned on the flexible member 14 such that the inflatable chamber 76 underlies the sole of the foot when the foot cuff is placed on the foot. The inflatable chamber 76 is adapted for receiving and retaining pressurized air for exerting compressive pressure on the foot during successive pressure application cycles, as will be understood by those skilled in this field. The opposing sheets 80, 84 of the bladder 56 are joined to one another in a suitable manner, such as by RF welding. Other ways of joining the sheets 80, 84 include sewing, adhesive, heat sealing, etc. It is understood that the bladder 56 can have other configurations within the scope of this invention. For example, the bladder may be formed from one or more sheets and/or may include more than one inflatable chamber.

The sole 60 of the bladder assembly 30 is a substantially rigid member positioned between the outer sheet 84 of the bladder 56 and the outer sheet 14B of the flexible member 14, and it extends generally lengthwise of the bottom of the foot when the foot cuff 10 is worn. The sole 60 provides a substantially rigid foundation against which the bladder 56 reacts during expansion. As a result, the expansion of the bladder 56 is directed toward the inner layer 14A of the flexible member 14 and the user's foot. The sole 60 is secured by suitable structure to maintain it in proper position relative to the bladder 56.

In the embodiment of FIGS. 1-5, the port 64 comprises a right-angle assembly, including an elbow member 90 and a tube 94. The elbow member 90 is of suitable material (e.g., plastic) and has passage 100 extending through it to permit flow of air from one end of the member 102, constituting its inlet end, to the opposite end 106 of the member, constituting its outlet end. The tube 94 is attached to the inlet end 102 of the elbow member 90 and projects through the opening 34 in the outer layer 14B of the flexible member 14 for connection to a compressor or the like for delivery of air under pressure to the elbow member. The outlet end 106 of the elbow member 90 is attached to the outer sheet 84 of the bladder 56 and is aligned with an opening 110 in the sheet 84 for delivery of air into the inflatable chamber 76 of the bladder, the outlet end 106 of the elbow member 90 and the bladder opening 110 thus defining the air outlet 72 of the port 64. The tube 94 is attached and sealed to the elbow member 90 by suitable means, such as heat sealing, RF welding, or adhesive, for example. The elbow member 90 is attached and sealed to the bladder 56 by similar means, e.g., heat sealing, RF welding, or adhesive. Other port configurations are within the scope of the present invention.

As can be seen in FIGS. 4 and 5, the bladder 56 has an internal air impingement surface 120 inside the inflatable chamber 76 opposing the air outlet 72 of the port 64. In particular, the air impingement surface 120 is the surface of the inner bladder sheet 80 facing the inflatable chamber 76. Noise attenuating means is provided on this surface 120 for reducing the noise generated by air entering the inflatable chamber 76 and impinging against the surface. In this particular embodiment, the noise attenuating means comprises a plurality of noise attenuating members 126 on the air impingement surface 120.

The noise attenuating members 126 dissipate energy during inflation of the inflatable bladder 56, resulting in reduced inflation noise. The surface of the protrusions 126 may comprise a thin membrane for absorbing energy of air impinging against the protrusions. For example, the protrusions 126 may be hollow and have a thin membrane exterior.

In the illustrated embodiment, the noise attenuating members 126 are integrally formed with the inner sheet 80 of the bladder 56 and comprise generally cylindrical protrusions (also designated 126) projecting into the inflatable chamber 76. The protrusions 126 are shown arranged in a generally symmetrical array. The protrusions 126 may be spaced approximately equally from each other. Other arrangements may be used. By way of example and not limitation, the protrusions 126 may have a diameter of approximately ¼ in. (0.64 cm) and be separated from each other by approximately ⅝ in. (1.59 cm) on center.

The noise attenuating members 126 may have other configurations within the scope of the present invention. For example, the noise attenuating members can cover the entire internal surface of the bladder 56 (i.e., the opposing surfaces of bladder sheets 80 and 84), or only the portion of the surface opposing the air outlet 72. The attenuating members 126 may have any suitable shape, such as concave, convex, oval and/or star-shaped. In addition, the attenuating members 126 may comprise part of a separate sheet or insert (not shown) that is encapsulated by the bladder sheets 80 and 84. The insert may be suitably secured (e.g., by welding) to the inner bladder sheet 80.

Figure 6:
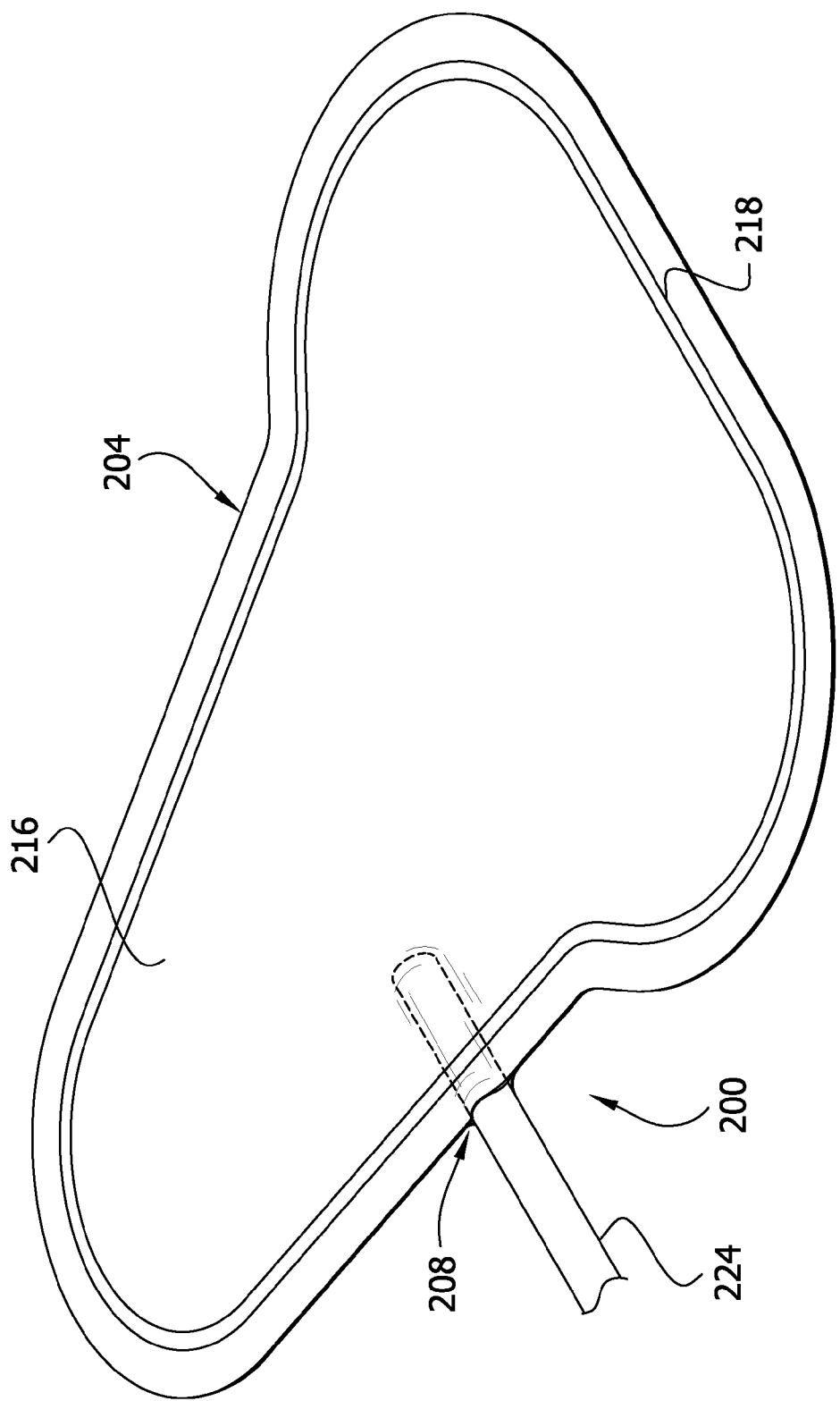
FIG. 6 is a bottom perspective of a second embodiment of a bladder assembly of the foot cuff.
Figure 7:
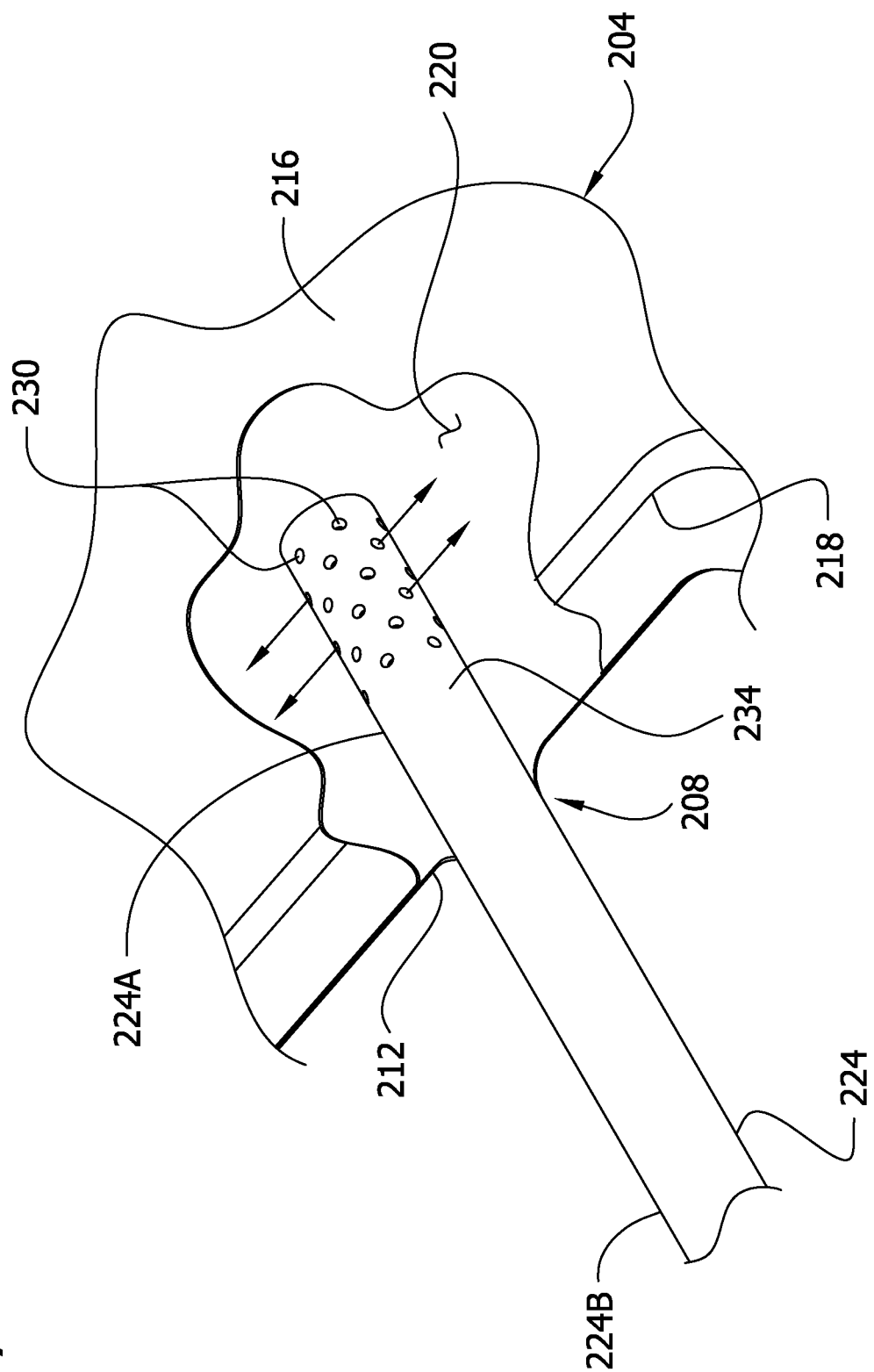
FIG. 7 is an enlarged perspective of a delivery tube on the bladder assembly of FIG. 6 with portions of the bladder assembly broken away to show a second embodiment of a noise attenuating means in accordance with the present disclosure.

FIGS. 6 and 7 show a second embodiment of a bladder assembly 200 of the present invention. The bladder assembly 200 comprises an inflatable bladder 204, a substantially rigid sole (not shown but similar to the sole 60 described in the first embodiment), and a port 208. The bladder 204 comprises inner and outer sheets 212, 216 secured to one another at their peripheries at 218 to define an internal inflatable chamber 220, as in the previous embodiment. The port 208 comprises a delivery tube 224 which extends between overlying edge margins of the inner and outer sheets 212, 216 of the bladder 204. The delivery tube 224 has an air outlet portion 224A inside the inflatable chamber 220 defining an air outlet of the port 224 and an air inlet portion 224B outside the inflatable chamber defining an air inlet of the port 224. The air inlet portion 224B extends through the opening 34 (see FIG. 2) or similar opening in the flexible member 14 and is configured to communicate with a source of air under pressure for delivering of air into the inflatable chamber 220 of the bladder 204 to inflate it. The delivery tube 224 is secured and sealed to the bladder 204 by suitable means, as by heat sealing, RF welding, adhesive or other means. Other ways of securing the delivery tube 224 to the bladder, such as adhesive, are within the scope of this invention.

The bladder assembly 200 includes noise attenuating means for reducing the noise generated by air entering the inflatable chamber 220. As shown best in FIG. 7, this means comprises a plurality of air flow apertures 230 in a sidewall 234 of the air outlet portion 224A of the delivery tube 224. The delivery tube 224 has a substantially uniform diameter along a segment of the delivery tube which extends continuously from a location in the inflatable chamber 220 to a location outside the inflatable chamber. The air flow apertures 230 are positioned on the delivery tube 224 downstream from the air inlet portion 224B of the delivery tube. In the illustrated embodiment, the air flow apertures 230 are spaced circumferentially around the sidewall 234 as well as axially along the sidewall. The outlet portion 224A of the delivery tube 224 terminates in a closed end, which may be blocked in a suitable manner (as by a cap or insert, not shown). As a result, air entering the delivery tube 224 is forced to flow into the inflatable chamber 220 of the bladder 204 through the air flow apertures 230 in a lateral direction relative to the longitudinal axis of the delivery tube. The air flow apertures 230 modify the air stream entering the bladder and reduce the noise due to inflation. By way of example and not limitation, the air outlet portion 224A of the delivery tube 224 may be approximately ½ in. (1.27 cm) long and have an internal diameter of approximately ¼ in. (0.64 cm). The air flow apertures 230 may be approximately 3⁄16 in. (0.48 cm) in diameter and be spaced from each other approximately 3⁄16 in. (0.48 cm) on center.

The air flow apertures 230 may have other sizes, spacings, and patterns within the scope of the present invention. Also, it is understood that other delivery tube configurations are within the scope of the present invention. For example, the outlet portion 224A of the delivery tube 224 can terminate in an open end for flow of air through the air flow apertures 230 and the open end of the delivery tube.

Having described the invention in detail, it will be apparent that modifications and variations are possible without departing from the scope of the invention defined in the appended claims.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above product without departing from the scope of the invention, it is intended that all matter contained in the above description and shown in the accompanying drawing[s] shall be interpreted as illustrative and not in a limiting sense.

What is claimed is:

1. A pneumatic compression garment comprising:
   a flexible member for placement on a limb of a human body;
   an inflatable bladder defining an inflatable chamber disposed within the flexible member;
   a port having an air inlet adapted for communication with a source of pressurized air and an air outlet in fluid communication with the inflatable chamber for delivery of air from the source of pressurized air into the inflatable chamber; and
   wherein the inflatable bladder has an air impingement surface comprising a plurality of noise attenuating members for reducing noise generated by air entering the inflatable chamber and impinging against said air impingement surface, at least one of said noise attenuating members positioned directly opposite the air outlet of the port.

2. The pneumatic compression garment of claim 1, wherein said noise attenuating members comprise protrusions projecting into the inflatable chamber.

3. The pneumatic compression garment of claim 2, wherein the protrusions are generally cylindrical.

4. The pneumatic compression garment of claim 1, wherein the port comprises a right-angle assembly, the right-angle assembly comprising an elbow member defining the air outlet and a tube received in the elbow member defining the air inlet.

5. The pneumatic compression garment of claim 4, wherein the inflatable bladder comprises two opposing sheets of flexible air-impermeable material and wherein the elbow member is affixed to an outside surface of one of the sheets and is in fluid communication with the inflatable chamber for delivery of air into the inflatable chamber.

6. The pneumatic compression garment of claim 5, wherein said noise attenuating members are integrally formed with one of the sheets of flexible air-impermeable material.

7. The pneumatic compression garment of claim 1, wherein the flexible member is configured for placement on a foot.

\* \* \* \* \*